US009237984B2

(12) United States Patent
Hawkins et al.

(10) Patent No.: US 9,237,984 B2
(45) Date of Patent: Jan. 19, 2016

(54) SHOCKWAVE NERVE THERAPY SYSTEM AND METHOD

(71) Applicant: SHOCKWAVE MEDICAL, INC., Fremont, CA (US)

(72) Inventors: Daniel Hawkins, Pleasanton, CA (US); John M. Adams, Snohomish, WA (US)

(73) Assignee: SHOCKWAVE MEDICAL, INC., Fremont, CA (US)

( * ) Notice: Subject to any disclaimer, the term of this patent is extended or adjusted under 35 U.S.C. 154(b) by 191 days.

(21) Appl. No.: 13/960,683

(22) Filed: Aug. 6, 2013

(65) Prior Publication Data
US 2014/0046229 A1 Feb. 13, 2014

Related U.S. Application Data

(60) Provisional application No. 61/681,853, filed on Aug. 10, 2012.

(51) Int. Cl.
*A61B 17/22* (2006.01)
*A61H 23/00* (2006.01)

(52) U.S. Cl.
CPC .......... *A61H 23/008* (2013.01); *A61B 17/2202* (2013.01); *A61B 17/22022* (2013.01); *A61B 2017/22021* (2013.01); *A61B 2017/22025* (2013.01); *A61B 2017/22028* (2013.01); *A61B 2017/22061* (2013.01); *A61B 2017/22062* (2013.01)

(58) Field of Classification Search
CPC . A61N 1/36117; A61N 1/056; A61B 17/225; A61B 17/2255; A61B 17/22004; A61B 17/22012; A61B 17/2202; A61B 2017/22051; A61H 23/008

USPC .............................. 607/44, 116; 606/2.5, 128
See application file for complete search history.

(56) References Cited

U.S. PATENT DOCUMENTS

| 7,925,352 | B2 * | 4/2011 | Stack et al. ..................... 607/44 |
| 2011/0166570 | A1 * | 7/2011 | Hawkins et al. ................ 606/41 |
| 2011/0257523 | A1 * | 10/2011 | Hastings .............. A61B 8/0891 600/439 |
| 2013/0150874 | A1 | 6/2013 | Kassab | |

FOREIGN PATENT DOCUMENTS

WO 2013/059735 A1 4/2013

OTHER PUBLICATIONS

Elashry, Osama, et al. Intracorporeal Electrohydraulic Lithotripsy of Ureteral and Renal Calculi Using Small Caliber (1.9F) Electrohydraulic Lithotripsy Probes. The Journal of Urology. Nov. 1996. vol. 156. p. 1581-1585.*

Connors et al., "Renal Nerves Mediate Changes in Contralateral Renal Blood Flow after Extracorporeal Shockwave Lithotripsy", Nephron Physiology, vol. 95, 2003, pp. 67-75.

(Continued)

*Primary Examiner* — Theodore Stigell
*Assistant Examiner* — Michael Carey
(74) *Attorney, Agent, or Firm* — Morrison & Foerster LLP

(57) ABSTRACT

Disclosed herein are intravascular systems and methods for modulating the activation of neural activity using shock wave devices. In one embodiment, the system is used to treat the nerves in the renal plexus. In a second embodiment, the system is used to treat the baroreceptors in the carotid sinus. In a preferred embodiment, the shock wave generator is in the form of electrodes mounted within an inflatable balloon.

16 Claims, 9 Drawing Sheets

(56) References Cited

OTHER PUBLICATIONS

Cleveland et al., "The Physics of Shock Wave Lithotripsy", Extracorporeal Shock Wave Lithotripsy Part IV, Chapter 38, 2012, pp. 315-332.

Gambihler et al., "Permeabilization of the Plasma Membrane of L1210 Mouse Leukemia Cells Using Lithotripter Shock Waves", The Journal of Membrane Biology, vol. 141, 1994, pp. 267-275.

Grassi et al., "Novel Antihypertensive Therapies: Renal Sympathetic Nerve Ablation and Carotid Baroreceptor Stimulation", Curr Hypertens Rep, vol. 14, 2012, pp. 567-572.

Kodama et al., "Shock Wave-Mediated Molecular Delivery into Cells", Biochimica et Biophysica Acta, vol. 1542, 2002, pp. 186-194.

Lauer et al., "Shock Wave Permeabilization as a New Gene Transfer Method", Gene Therapy, vol. 4, 1997, pp. 710-715.

* cited by examiner

SHOCKWAVE NERVE THERAPY SYSTEM AND METHOD

CROSS-REFERENCE TO RELATED APPLICATIONS

This application claims the benefit of U.S. Provisional Application 61/681,853 filed on Aug. 10, 2012, which is hereby incorporated by reference in its entirety.

BACKGROUND

Chronic hypertension may be the cause of various disease states, including heart failure and stroke. Elevated blood pressure may be controlled using pharmacological agents, such as diuretics, beta-blockers, angiotensin converting enzyme (ACE) inhibitors, and the like. However, the efficacy of such pharmacological interventions may vary greatly, and for some patients, may be insufficient to reduce their blood pressure to a normal range.

Non-pharmacological treatment options may include modulating the activity of neurons that play a role in regulating blood pressure. For example, modulating the neural activity of the renal plexus may help to reduce blood pressure where pharmacological agents are ineffective and/or insufficient. Devices for renal denervation may include devices that ablate (either by heating or freezing) the renal plexus. Additionally or alternatively, baroreceptors (e.g., the baroreceptors in the carotid sinus) may be activated to help reduce blood pressure. Additional devices and methods for modulating these neural structures may be desirable as part of a treatment plan for chronic hypertension.

BRIEF SUMMARY

Disclosed herein are intravascular systems and methods for modulating the activation of neural activity using shock wave devices. Such systems and methods may be used to modulate the activity of the renal plexus and/or baroreceptors of the carotid sinus for the treatment of hypertension. Intravascular shock wave devices may be introduced into a renal artery in order to reduce and/or block activation of the renal plexus. The application of shock waves to a renal plexus may temporarily deactivate (e.g., by causing neurapraxia) so that a practitioner can determine whether such treatment would result in blood pressure reduction. Once it has been determined that deactivating the renal plexus attains the desired effect, the practitioner may apply shock waves to permanently ablate the renal plexus (i.e., renal denervation). Alternatively or additionally, shock wave devices may be advanced through the vasculature to the carotid sinus for stimulating the baroreceptors. Shock waves may create positive pressure pulses that may be sensed by the baroreceptors, which then signal the nervous system via the baroreflex to reduce blood pressure.

One variation of a method for nerve therapy may comprise advancing a shock wave device within a renal artery, where the shock wave device comprises an elongate body having a guide wire lumen and a shock wave generator coupled to the elongate body, and initiating a shock wave from the shock wave generator at a first location in the renal artery adjacent to a renal plexus to impinge upon a wall of the renal artery to at least partially block activation of a renal plexus. The shock wave device may further comprise a balloon sealably enclosing a portion of the elongate body, and the shock wave generator may be located within the balloon. The method may optionally comprise inflating the balloon with a liquid before initiating a shock wave from the shock wave generator. In some variations, the method may also comprise initiating a plurality of shock waves at the first location in the renal artery. After initiating one or more shock waves at the first location, the method may further comprise initiating a shock wave from the shock wave generator at a second location in the renal artery. Initiating a shock wave at a second location may comprise moving the shock wave generator along a longitudinal axis of the elongate body from the first location to the second location, and/or rotating the shock wave generator around a longitudinal axis of the elongate body from the first location to the second location. In some variations, initiating a shock wave at the second location may comprise deflating the balloon of the shock wave device, moving the shock wave device to the second location inflating the balloon with a liquid, and initiating a shock wave from the shock wave generator at the second location.

In some variations, the shock wave generator of a shock wave device may comprise at least one electrode. Optionally, the shock wave device may comprise a second shock wave generator, where the first shock wave generator is at the first location and the second shock wave generator is at a second location. A method of using a shock wave device comprising a first shock wave generator and a second shock wave generator may comprise initiating a shock wave from the first shock wave generator at a first location and initiating the second shock wave generator at a second location. Optionally, a shock wave may be initiated at the first location from the first shock wave generator and a shock wave may be initiated at the second location from the second shock wave generator at substantially the same time. In some variations, a shock wave generator may comprise an insulating layer wrapped around a portion of the elongate body, said layer having a first aperture therein, an inner electrode carried within the elongate body and aligned with the first aperture of the insulating layer, and an outer electrode mounted on the insulating layer and having a first aperture coaxially aligned with the first aperture in the insulating layer and arranged so that when a voltage is applied across the electrodes, a shockwave will be initiated therebetween.

Another variation of a method for nerve therapy may comprise advancing a shock wave device within a carotid sinus, where the shock wave device comprises an elongate body having a guide wire lumen and a shock wave generator coupled to the elongate body, and initiating a shock wave from the shock wave generator at a first location in the renal artery adjacent to a renal plexus to impinge upon and activate baroreceptors located in the carotid sinus. The shock wave device may further comprise a balloon sealably enclosing a portion of the elongate body, and the shock wave generator may be located within the balloon. The method may optionally comprise inflating the balloon with a liquid before initiating a shock wave from the shock wave generator. In some variations, the method may also comprise initiating a plurality of shock waves at the first location in the carotid sinus. After initiating one or more shock waves at the first location, the method may further comprise initiating a shock wave from the shock wave generator at a second location in the carotid sinus. Initiating a shock wave at a second location may comprise moving the shock wave generator along a longitudinal axis of the elongate body from the first location to the second location, and/or rotating the shock wave generator around a longitudinal axis of the elongate body from the first location to the second location. In some variations, initiating a shock wave at the second location may comprise deflating the balloon of the shock wave device, moving the shock wave device to the second location inflating the balloon with a liquid, and initiating a shock wave from the shock wave generator at the second location.

In some variations, the shock wave generator of a shock wave device may comprise at least one electrode. Optionally, the shock wave device may comprise a second shock wave generator, where the first shock wave generator is at the first location and the second shock wave generator is at a second location. A method of using a shock wave device comprising a first shock wave generator and a second shock wave generator may comprise initiating a shock wave from the first shock wave generator at a first location in the carotid sinus and initiating the second shock wave generator at a second location in the carotid sinus. Optionally, a shock wave may be initiated at the first location from the first shock wave generator and a shock wave may be initiated at the second location from the second shock wave generator at substantially the same time. In some variations, a shock wave generator may comprise an insulating layer wrapped around a portion of the elongate body, said layer having a first aperture therein, an inner electrode carried within the elongate body and aligned with the first aperture of the insulating layer, and an outer electrode mounted on the insulating layer and having a first aperture coaxially aligned with the first aperture in the insulating layer and arranged so that when a voltage is applied across the electrodes, a shockwave will be initiated therebetween.

DETAILED DESCRIPTION

Figure 1A:
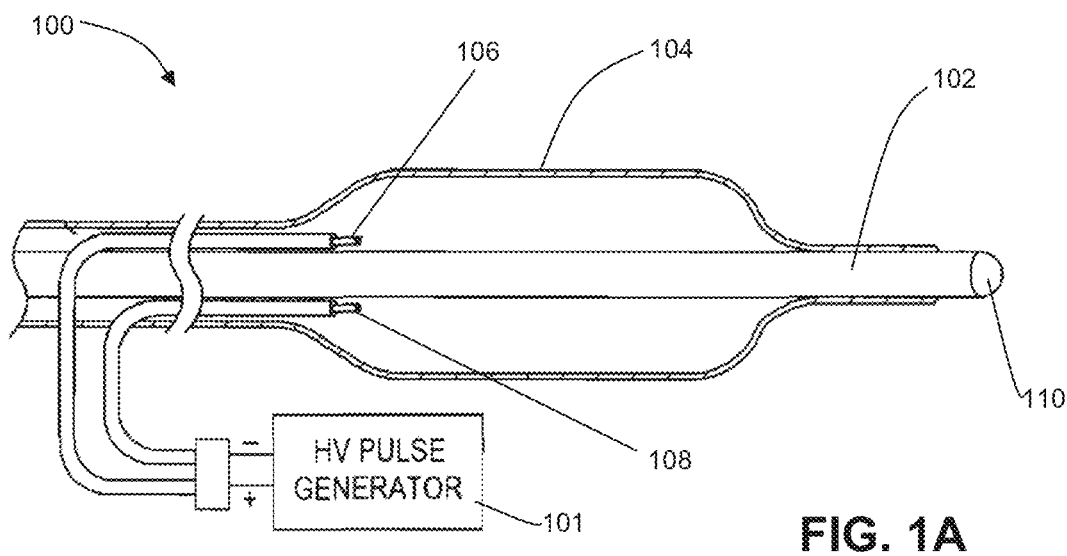
FIGS. 1A-1C depict different variations of shock wave devices that may be used for intravascular modulation of neural activity.

Disclosed herein are intravascular systems and methods for modulating the activity of the renal plexus and/or baroreceptors of the carotid sinus using shock wave devices. Shock waves may generate mechanical forces (such as pressure pulses) that may impinge on the neural structure, which may affect its neural activity such that systemic blood pressure is reduced. Such neural effects may be temporary, which may help a practitioner decide whether to implement hypertension treatment plans that include permanent and/or constant neural modulation. Although the methods and devices described below relate to neuromodulation of the renal plexus and/or baroreceptors of the carotid sinus, it should be understood that these methods and devices may be used to modulate the activity of any neural target (e.g., sacral nerve, tibial nerve, any peripheral nerves involved in the transmission of pain sensations, arterial and/or low-pressure baroreceptors, etc.).

In some variations, a method may comprise advancing an intravascular shock wave device into a renal artery and generating shock waves in the proximity of the renal plexus to reduce and/or block activation of the renal plexus. Without wishing to be bound by theory, pressure pulses generated by shock waves may interrupt the neural activity of the renal plexus by non-uniformly straining the neural filaments and/or nerves of the renal plexus. Such non-uniform strain may give rise to shear forces that may damage these filaments and/or nerves, thereby reducing or blocking their activation. Depending on the magnitude of these mechanical forces sustained by the structures of the renal plexus, interruption of their neural activity may be temporary or permanent. For example, neurapraxia of the renal plexus may be induced by generating shock waves that result in pressure pulses with relatively low magnitudes of force and/or frequency. This type of temporary impairment of the renal plexus may be used as part of a treatment plan to determine whether or not renal denervation by ablating the renal plexus would provide the desired clinical result. Once it has been determined that reducing or blocking activation of the renal plexus would be effective in reducing blood pressure, renal denervation may be considered as part of a long term treatment plan. Methods of renal denervation may comprise generating shock waves in the renal artery adjacent to the renal plexus, where the shock waves may give rise to high magnitude and/or high frequency pressure pulses that permanently damage the filaments and/or nerves of the renal plexus. Alternatively or additionally, renal denervation may be performed using other devices and methods (e.g., cryo-ablation, irreversible electroporation, RF heating, etc.).

Methods for treating hypertension may optionally comprise advancing intravascular shock wave devices to the carotid sinus and generating shock waves that may stimulate the baroreceptors of the carotid sinus. Stimulating the baroreceptors of the carotid sinus may trigger the baroreflex pathway to take steps toward the reduction of blood pressure. Generating shock waves that result in positive pressure pulses with relatively low magnitudes of force and/or frequency that may provide sufficient stimulation of the baroreceptors to trigger the reduction of blood pressure. Once it has been determined that such stimulation of the carotid sinus baroreceptors is effective in reducing blood pressure, a practitioner may prescribe constant and/or persistent stimulation of the baroreceptors by an implanted device as part of a long term treatment plan.

Different variations of intravascular shock wave devices may be used to modulate the neural activity of the renal plexus and/or carotid sinus baroreceptors. Shock wave devices may comprise one or more electrodes attached to an elongate body, where the electrodes are enclosed within a fluid-filled balloon that is sealably attached to the elongate body. A shock wave may be formed when a high voltage pulse is applied across the two electrodes. The pressure pulse resulting from the shock wave may propagate through the fluid (e.g., a liquid comprising saline and/or a contrast agent) to impinge on the wall of the balloon, which may in turn transmit that force to the targeted neural structure. The balloon may be made of a non-compliant and electrically insulated material, which may help to prevent expansion of the balloon during shock wave generation and protect the patient from any electrical shocks. Limiting expansion of the balloon during shock wave generation may help protect the renal artery from barotrauma otherwise caused by a balloon expanding under the force of steam bubbles formed therein by the electrohydraulic shock wave generator. In addition, the balloon may be sized equal to or smaller than the renal artery. The shock waves travel through the balloon wall, the blood and tissue of the renal artery and impinge on the renal plexus. While the shock wave devices described and depicted below comprise a balloon sealably coupled to the elongate body, it should be understood that in other variations, shock wave devices may not have any balloons, or may have a balloon having one or more apertures such that blood may flow through the balloon during treatment.

The magnitude of the shock waves may be controlled by adjusting the magnitude, current, frequency, and/or duty cycle of the voltage pulses applied across the electrodes. Although the shock wave devices described here generate shock waves based on high voltage electrodes, it should be understood that a shock wave device additionally or alternatively comprise a laser shockwave generator inside the balloon.

Figure 1B:
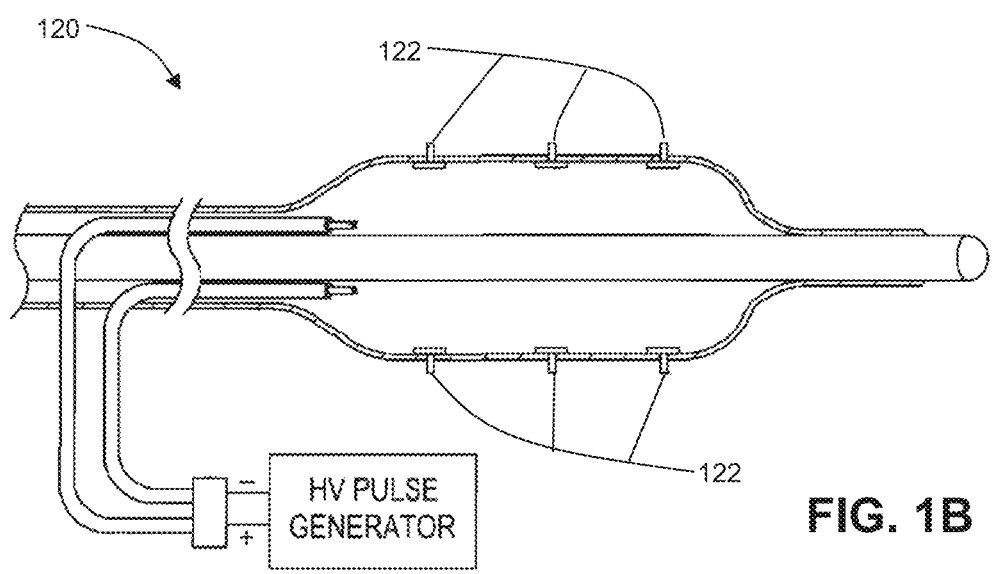
Figure 1C:
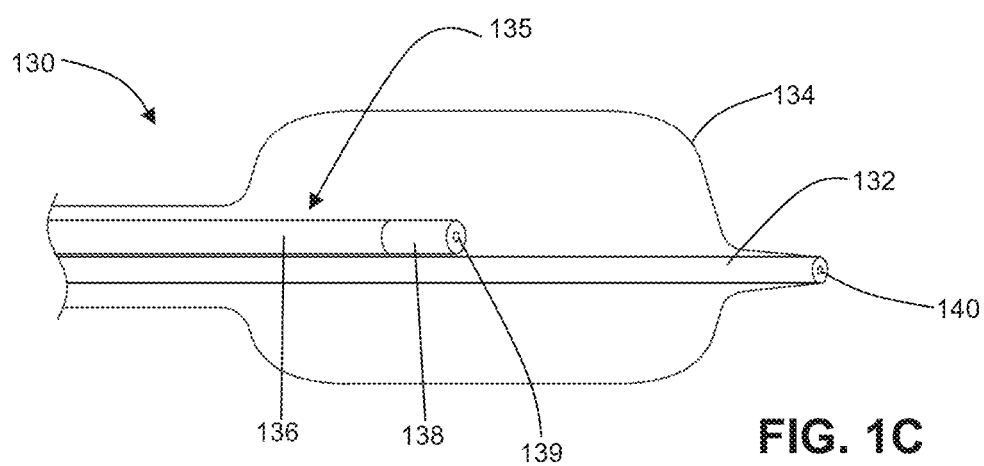

FIGS. 1A-1C depict different variations of shock wave devices that may comprise one or more electrodes at least partially surrounded by one or more insulating sleeves or shafts, where the insulating sleeve(s) or shaft(s) may be attached to an elongate body and a conductive tip of the electrode is exposed. FIG. 1A depicts a shock wave device 100 comprising an elongate body 102, an inflatable balloon 104 sealably attached to a distal portion of the elongate body, a first electrode 106 surrounded by an insulating sleeve and attached to the elongate body 102, a second electrode 108 surrounded by an insulating sleeve and attached to the elongate body 102. The elongate body 102 may comprise a longitudinal guide wire lumen 110 therethrough. The electrodes may be enclosed within the balloon 104, which may be inflated with a liquid. The first electrode 106 may be connected to a positive terminal of a high voltage pulse generator 101 and the second electrode 108 may be connected to a negative terminal of the high voltage pulse generator 101 to generate a shock wave between the two electrodes. FIG. 1B depicts another variation of a shock wave device 120 that may comprise all the elements of the shock wave devices 100, and additionally comprise one or more stand-off structures 122 on the external surface of the balloon. The stand-off structures may be studs, ridges, protrusions, ribs, and the like. The stand-off structures 122 may a form mechanical stress riser on the balloon surface and may mechanically conduct the force of the shock wave from within the balloon to the vascular wall and/or neural structure(s). FIG. 1C depicts another variation of a shock wave device 130 that may comprise an elongate body 132, a fluid-filled balloon 134 sealably attached to a distal portion of the elongate body 132, and a shock wave generator 135 coupled to the elongate body 132 within the balloon. The elongate body 132 may comprise a guide wire lumen 140 therethrough. The shock wave generator 135 may comprise a shaft 136, a first inner electrode 139 that is located along a central longitudinal axis of the shaft and a second outer electrode 138 that is a ring surrounding the first inner electrode 139. There may be an insulating material between the first and second electrodes. In some variations, the first inner electrode 139 may be aligned with the center of the second outer electrode 138 (i.e., in a coaxial configuration). The first and second electrodes may be connected to the positive and negative terminals of a voltage pulse generator (not shown).

Figure 2A:
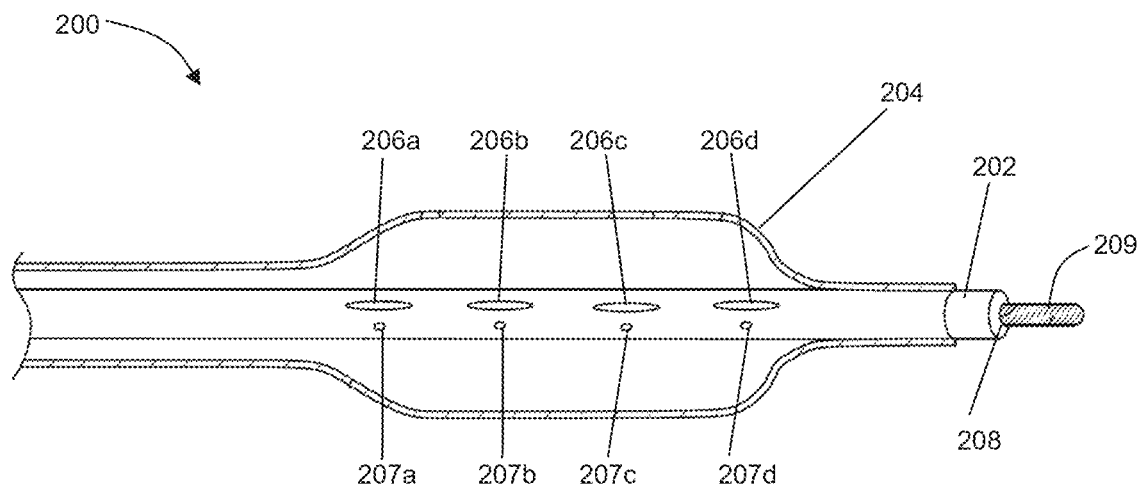
FIGS. 2A-2D depict additional variations of shock wave devices that may be used for intravascular modulation of neural activity.
Figure 2B:
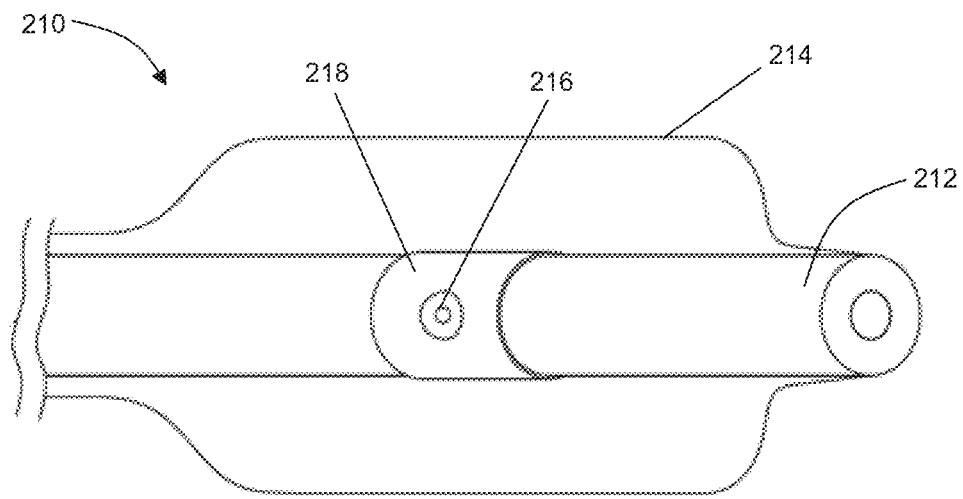
Figure 2C:
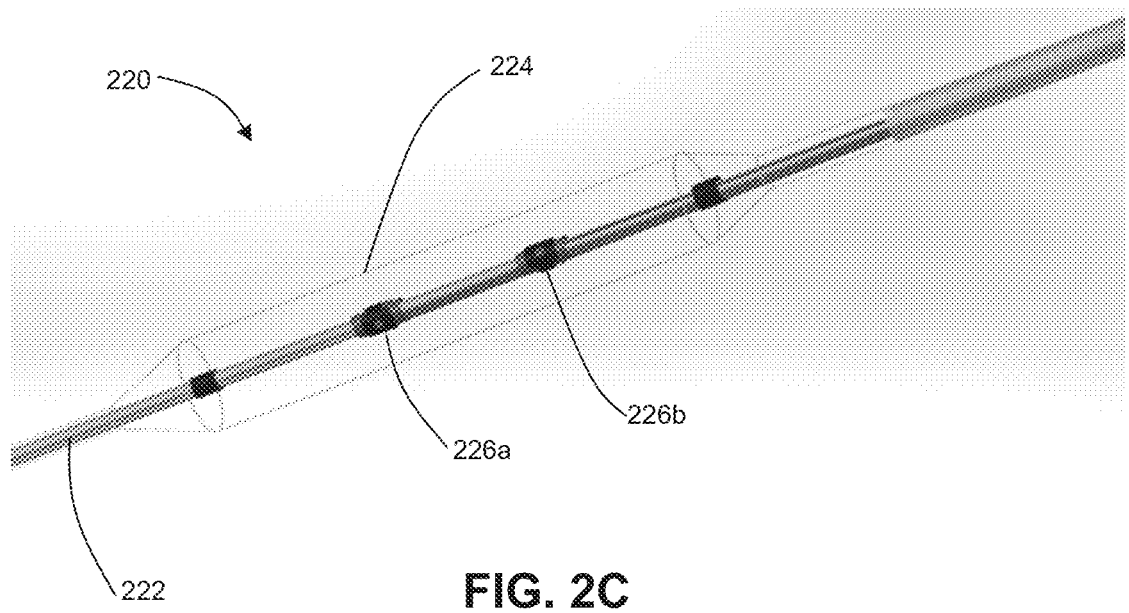
Figure 2D:
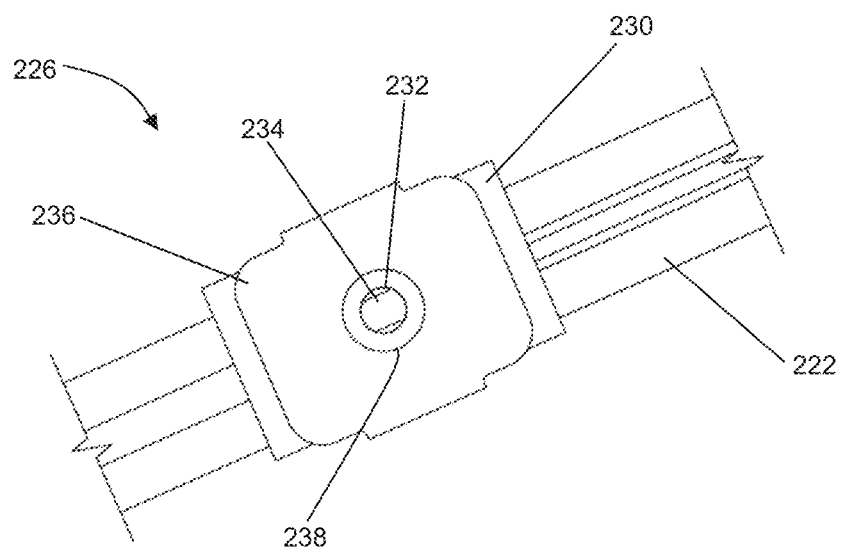

FIGS. 2A-2D depict other variations of shock wave devices that may comprise low-profile shock wave electrodes that are located along the side of an elongate body. FIG. 2A depicts one variation of a shock wave device 200 comprising an elongate body 202, a fluid-filled balloon 204 sealably enclosed over a distal portion of the elongate body, one or more pairs of electrodes located along the side of the elongate body and within the balloon. The elongate body 202 may be made of an electrically insulated material and may comprise a guide wire lumen 208 therethrough for the passage of a guide wire 209. The balloon may be made of a non-compliant and electrically insulated material. Each electrode pair may comprise a first electrode 206 that may be connected to a positive terminal of a voltage pulse generator (not shown) and a second electrode 207 that may be connected to a negative terminal of the voltage pulse generator. When a high voltage pulse is applied across electrodes in a pair (e.g., across electrodes 206a and 207a, 206b and 207b, etc.), a shock wave may be generated. Each pair of electrodes may be activated separately and/or independently from the other pairs, or maybe activated simultaneously. FIG. 2B depicts another variation of a shock wave device 210 that may comprise an elongate body 212, a fluid-filled balloon 214 sealably enclosed over a distal portion of the elongate body, a first inner electrode 216 and a second outer electrode 218 that may be a ring with an opening that is centered over the first inner electrode. The elongate body 212 may be made of an electrically insulated material and may have a guide wire lumen therethrough. The inner electrode and outer electrode are located along the portion of the elongate body that is sealably enclosed by the balloon. The first inner electrode 216 may be connected to a positive terminal of a voltage pulse generator (not shown) and the second electrode 218 may be connected to a negative terminal of the voltage pulse generator. FIGS. 2C and 2D depict another variation of a shock wave device 220 that may comprise an elongate body 222, a fluid-filled balloon 224 sealably enclosed over a distal portion of the elongate body, a first shock wave electrode assembly 226a and a second shock wave electrode assembly 226b. Each shock wave electrode assembly may comprise an insulating layer 230 wrapped around a portion of the elongate body 222, an inner electrode 234 carried within the elongate body and aligned with a first aperture 232 of the insulating layer 230, and an outer electrode 236 mounted on the insulating layer 230 and having a first aperture 238 that is coaxially aligned with the first aperture 232 of the insulating layer. The inner electrode 234 may be connected to the positive terminal of a high voltage pulse generator and the outer electrode 236 may be connected to a negative terminal of the pulse generator so that when a voltage pulse is applied across the inner and outer electrodes, a shock wave may be generated between them. The electrodes of any of the above shock wave devices may be movable within the balloon. For example, the electrodes may be rotated around the longitudinal axis of the elongate body, and/or may translate along the longitudinal axis of the elongate body. Such mobility of the shock wave generator (i.e., electrodes) within the balloon may allow for the application and/or focusing of shock waves to different tissue regions without deflating and inflating and/or otherwise moving the balloon within the vasculature. Additional descriptions of intravascular shock wave devices and systems that may be used for modulating the neural activity of the renal plexus and/or baroreceptors of the carotid sinus may be found in co-owned and co-pending U.S. Pub. No. 2009/0312768 filed Jun. 11, 2009, U.S. Pub. No. US 2014/0005576, filed Jun. 27, 2012, and U.S. Pub. No. 2014/0039513, filed Mar. 14, 2013, which are hereby incorporated by reference in their entirety.

Figure 3A:
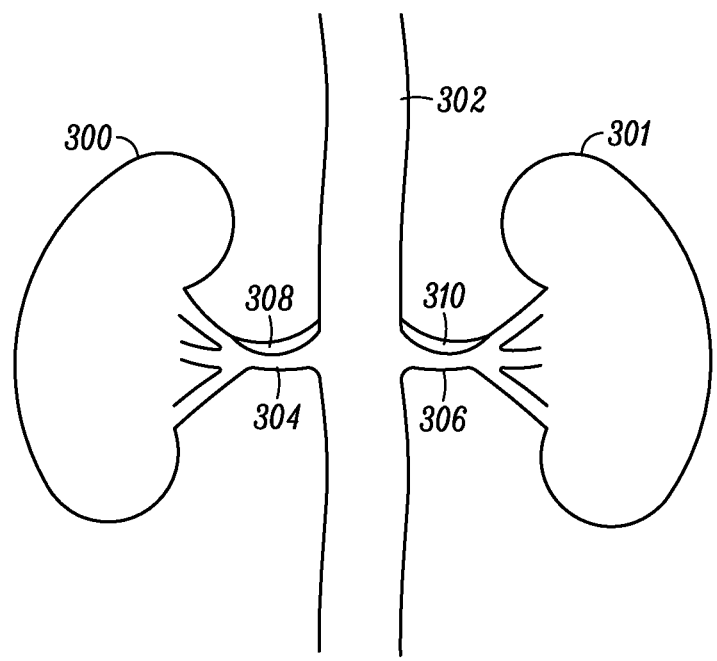
FIG. 3A depicts a schematic view of the kidneys, renal arteries, and renal plexus.
Figure 3B:
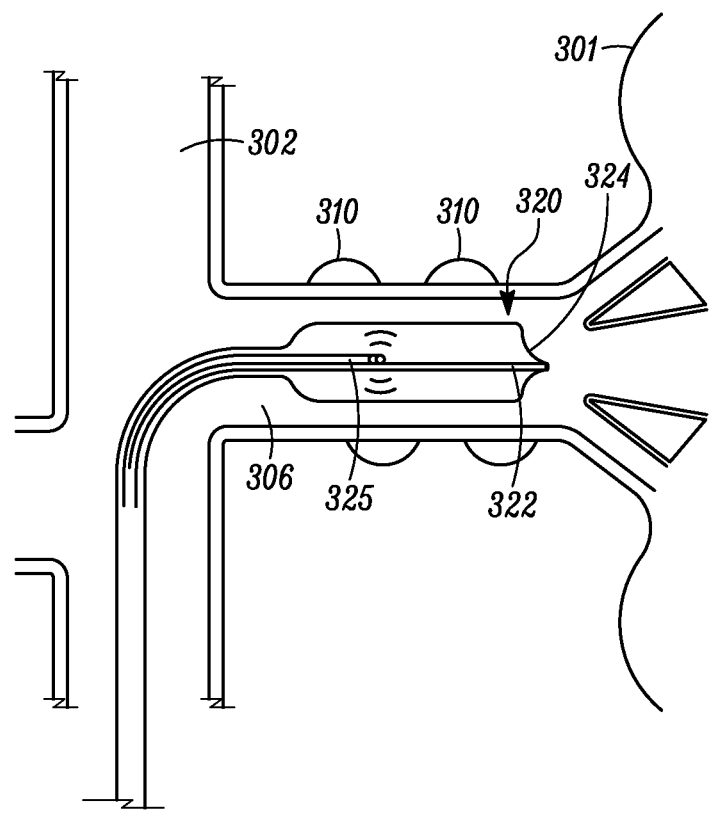
FIG. 3B depicts an intravascular shock wave device within the renal artery adjacent to the renal plexus.

Any of the shock wave devices described above may be used to intravascularly modulate the neural activity of a renal plexus. FIG. 3A schematically depicts a left kidney 300 and right kidney 301, an aorta 302 and left 304 and right 306 renal arteries branching from the aorta. FIG. 3A also depicts a left renal plexus 308 and a right renal plexus 310 that wrap along a portion of the left and right renal arteries. FIG. 3B schematically depicts a shock wave device 320 placed in the right renal artery 306 at location in proximity (e.g., adjacent) to the right renal plexus 310. The shock wave device 320 may comprise an elongate body 322, a fluid-filled balloon 324, and a shockwave generator 325 enclosed within the balloon. For example, the shock wave device may be similar to the device described and depicted in FIG. 1C. Shock waves generated within the balloon 324 by the shock wave generator 325 may propagate through the liquid within the balloon and impinge on a filament and/or nerve of the right renal plexus 310. Depending on the amount and frequency of the force generated by the shock wave(s), the neural activity of the renal plexus may be temporarily and/or permanently affected. For example, a series of high intensity shock waves may be delivered to the renal plexus in this manner causing temporary or long term nerve dysfunction.

Figure 4A:
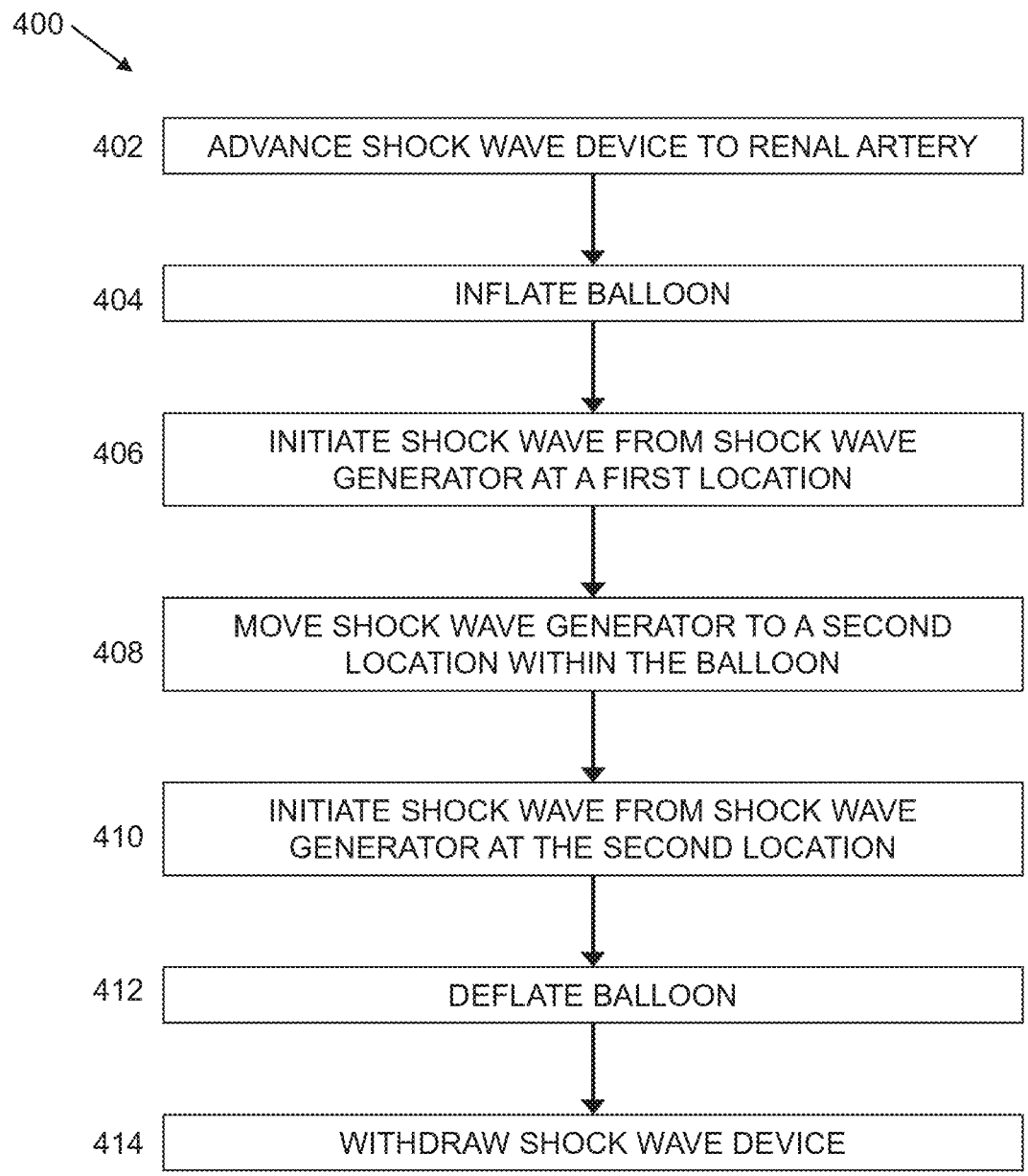
FIGS. 4A and 4B are flowchart representations of methods for modulating activation of the renal plexus using an intravascular shock wave device.

FIG. 4A is a flowchart depiction of one variation of a method 400 for modulating the neural activity of the renal plexus. The method 400 may comprise advancing the shock wave device to the renal artery (402) to a location that is adjacent to a renal plexus. In some variations, advancing the shock wave device may comprise advancing a guide wire to the desired location and advancing the shock wave device over the guide wire via the guide wire lumen in the elongate body. After the shock wave device has been advanced (with the balloon deflated) to the desired location, the balloon may be inflated with a liquid (404), such as saline and/or a contrast agent. A shock wave may then be initiated by the shock wave generator at a first location (406), for example, by applying a voltage pulse across the electrodes of the shock wave generator. One or more shock waves may be generated at the first location. Once a desired amount of shock wave force has been applied to the renal plexus from the first location, the shock wave generator may be moved to a second location within the balloon (408). One or more shock waves may then be initiated by the shock wave generator at the second location (410). Once a desired amount of shock wave force has been applied to the renal plexus from the second location, the shock wave generator may be moved to other locations along the renal artery to affect other regions of the renal plexus. The blood pressure of the patient may be monitored during the treatment session, and/or may continue to be monitored after the treatment session. At the completion of the treatment session, the balloon may be deflated (412) and withdrawn from the renal artery (414). Optionally, the above method may be repeated for treatment of the contralateral renal plexus 308.

Figure 4B:
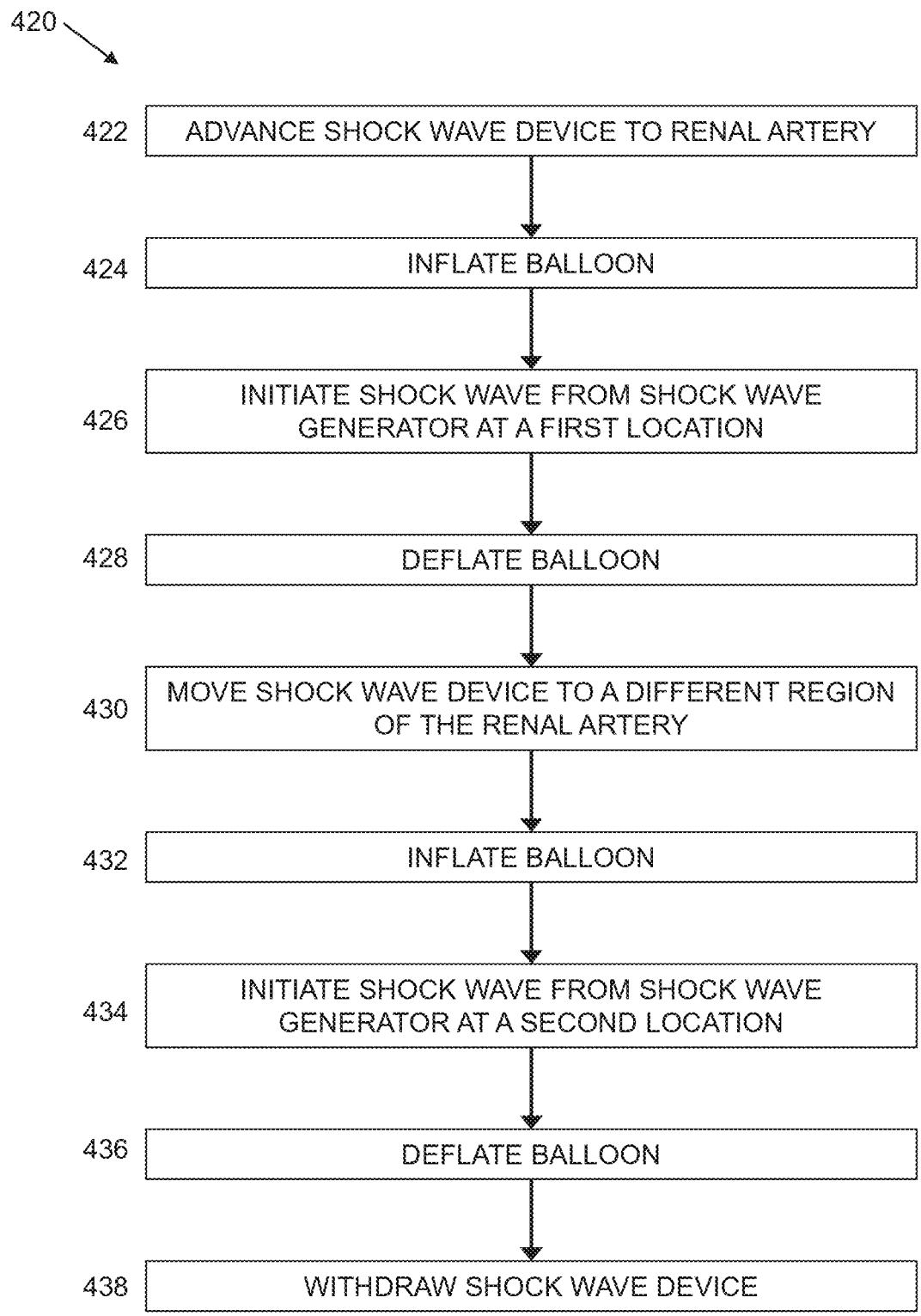

Another variation of a method 420 for modulating the activation of a renal plexus is depicted in FIG. 4B. The method 420 may comprise advancing the shock wave device to the renal artery (422) to a location that is adjacent to a renal plexus. In some variations, advancing the shock wave device may comprise advancing a guide wire to the desired location and advancing the shock wave device over the guide wire via the guide wire lumen in the elongate body. After the shock wave device has been advanced (with the balloon deflated) to the desired location, the balloon may be inflated with a liquid (424). A shock wave may then be initiated by the shock wave generator at a first location (426), for example, by applying a voltage pulse across the electrodes of the shock wave generator. One or more shock waves may be generated at the first location. Once a desired amount of shock wave force has been applied to the renal plexus from the first location, the balloon may be deflated (428) and the shock wave device may be moved to a different region of the renal artery (430). The balloon may then be inflated (432) and one or more shock waves may then be initiated by the shock wave generator at a second location (434). Optionally, the shock wave generator may be moved within the balloon. The blood pressure of the patient may be monitored during the treatment session, and/or may continue to be monitored after the treatment session. At the completion of the treatment session, the balloon may be deflated (436) and withdrawn from the renal artery (438). Optionally, the above method 420 may be repeated for treatment of the contralateral renal plexus.

Some methods may additionally comprise renal denervation after shock wave treatment, as may be desirable. Renal denervation may be achieved using the shock wave devices described herein by increasing the magnitude, current, frequency, and/or duty cycle of the voltage pulse generator so that the shock wave generators within the balloon apply sufficient amounts of force to permanently damage a portion of the renal plexus. Alternatively or additionally, other methods and devices for renal denervation may be used. For example, if a practitioner determines that modulating the activity of the renal plexus (e.g., blocking and/or reducing activation of the renal plexus) substantially reduces the patient's blood pressure, s/he may prescribed long-term deactivation of the renal plexus (e.g., by renal denervation) as part of the treatment plan for alleviating symptoms of hypertension.

Figure 5:
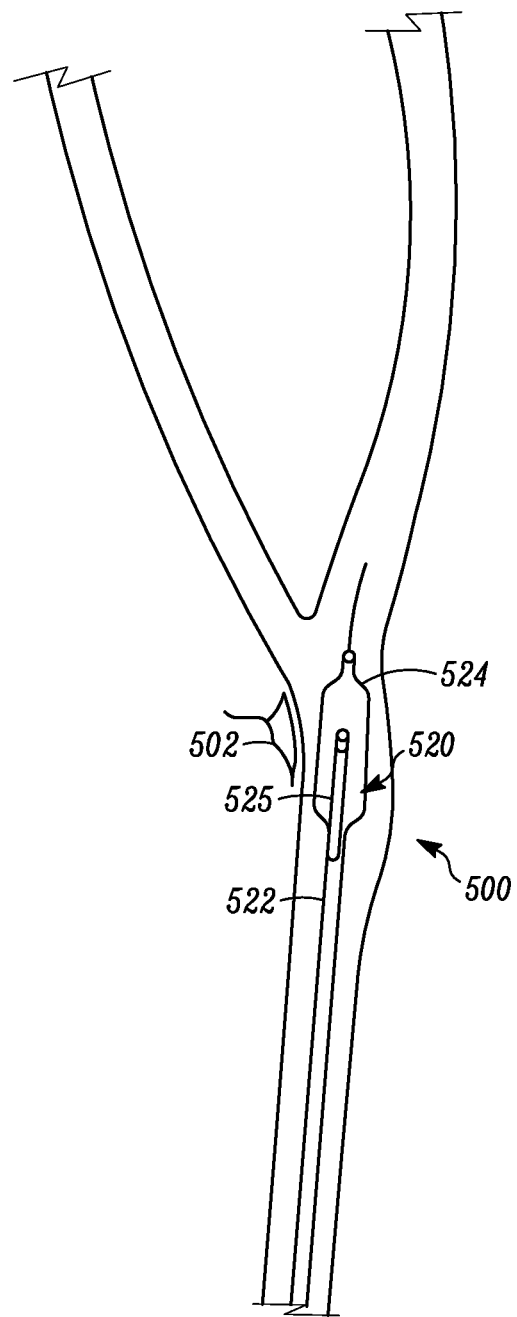
FIG. 5 depicts a schematic view of a carotid sinus and associated baroreceptors.

Any of the shock wave devices described above may be used to intravascularly modulate the neural activity of the carotid sinus baroreceptors. FIG. 5 schematically depicts a shock wave device 520 placed in the carotid sinus 500 in proximity (e.g., adjacent) to the baroreceptors 502. The shock wave device 520 may comprise an elongate body 522, a fluid-filled balloon 524, and a shockwave generator 525 enclosed within the balloon. For example, the shock wave device may be similar to the device described and depicted in FIG. 1C. Shock waves generated within the balloon 524 by the shock wave generator 525 may create positive pressure pulses/waves that may propagate through the liquid within the balloon and act to stretch the wall of the sinus. Stretching the wall of the carotid sinus may in turn activate the baroreceptors along the sinus wall. Increasing the amount and frequency of the force generated by the shock wave(s) may similarly increase the stimulation and activity of the baroreceptors, which may help to reduce the blood pressure of the patient.

Figure 6A:
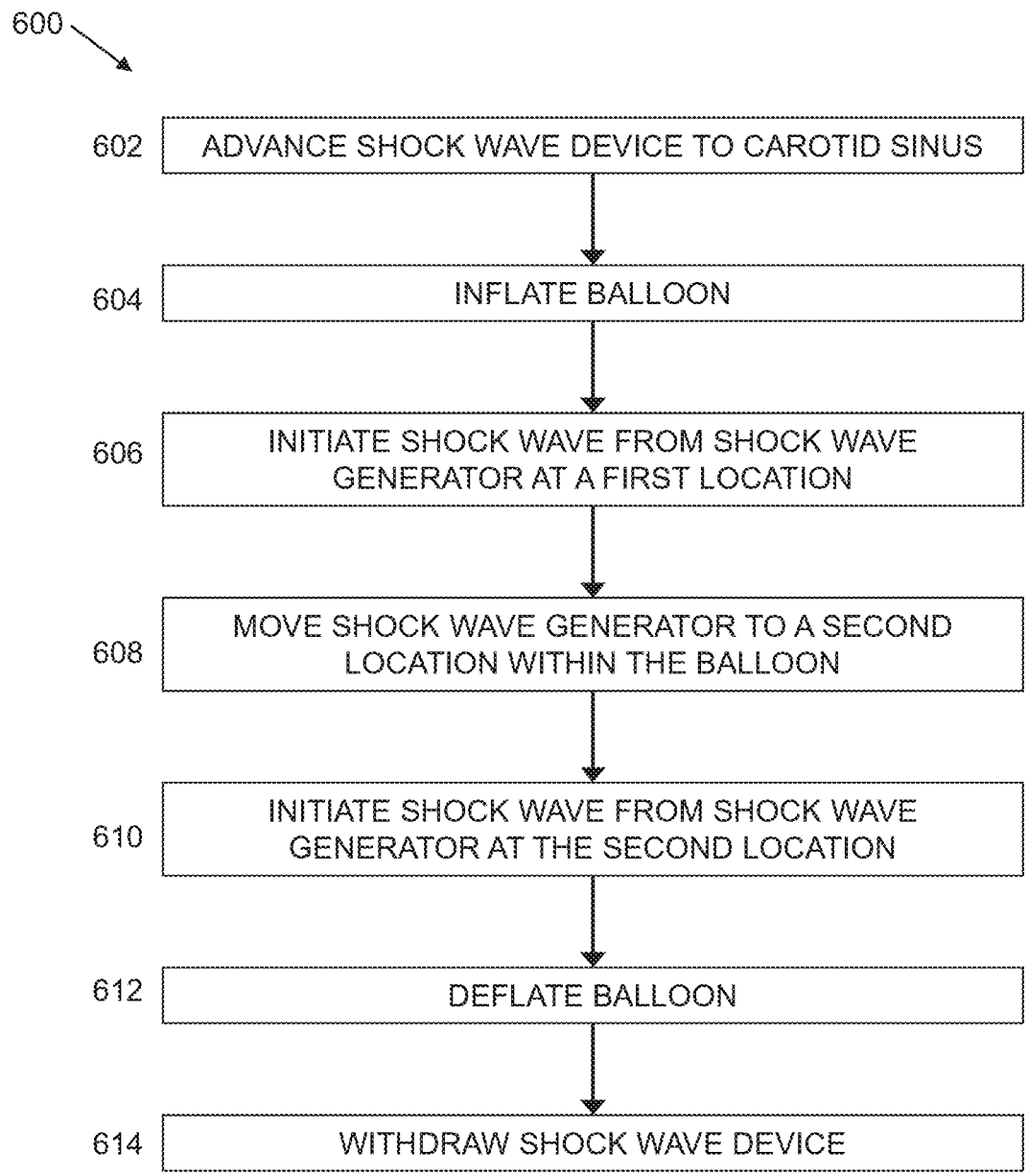
FIGS. 6A and 6B are flowchart representations of methods for modulating activation of the carotid sinus baroreceptors using an intravascular shock wave device.

FIG. 6A is a flowchart depiction of one variation of a method 600 for stimulating the neural activity of the carotid sinus baroreceptors. The method 600 may comprise advancing the shock wave device to the carotid sinus (602) to a location in the carotid sinus. In some variations, advancing the shock wave device may comprise advancing a guide wire to the desired location and advancing the shock wave device over the guide wire via the guide wire lumen in the elongate body. After the shock wave device has been advanced (with the balloon deflated) to the desired location, the balloon may be inflated with a liquid (604). A shock wave may then be initiated by the shock wave generator at a first location (606), for example, by applying a voltage pulse across the electrodes of the shock wave generator. One or more shock waves may be generated at the first location. Once a desired amount of shock wave force has been applied to the baroreceptors of the carotid sinus from the first location, the shock wave generator may be moved to a second location within the balloon (608). One or more shock waves may then be initiated by the shock wave generator at the second location (610). Once a desired amount of shock wave force has been applied to the baroreceptors of the carotid sinus from the second location, the shock wave generator may be moved to other locations in the carotid sinus. The blood pressure of the patient may be monitored during the treatment session, and/or may continue to be monitored after the treatment session. At the completion of the treatment session, the balloon may be deflated (612) and withdrawn from the carotid sinus (614).

Figure 6B:
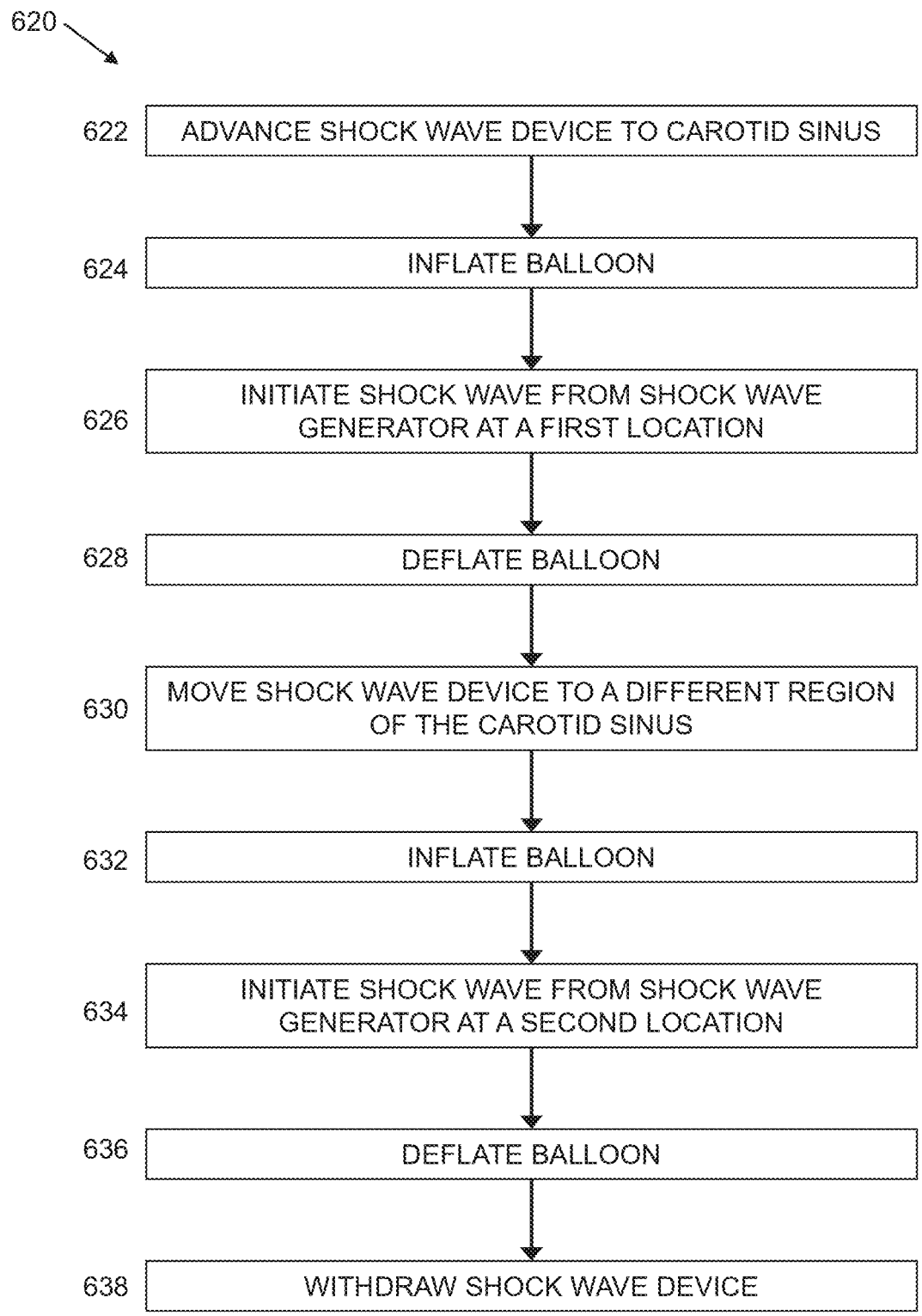

Another variation of a method 620 for modulating the activation of the baroreceptors of the carotid sinus is depicted in FIG. 6B. The method 620 may comprise advancing the shock wave device to the carotid sinus (622). In some variations, advancing the shock wave device may comprise advancing a guide wire to the desired location and advancing the shock wave device over the guide wire via the guide wire lumen in the elongate body. After the shock wave device has been advanced (with the balloon deflated) to the desired location, the balloon may be inflated with a liquid (624). A shock wave may then be initiated by the shock wave generator at a first location (626), for example, by applying a voltage pulse across the electrodes of the shock wave generator. One or more shock waves may be generated at the first location. Once a desired amount of shock wave force has been applied to the baroreceptors of the carotid sinus from the first location, the balloon may be deflated (628) and the shock wave device may be moved to a different region of the carotid sinus (630). The balloon may then be inflated (632) and one or more shock waves may then be initiated by the shock wave generator at a second location (634). Optionally, the shock wave generator may be moved within the balloon. The blood pressure of the patient may be monitored during the treatment session, and/or may continue to be monitored after the treatment session. At the completion of the treatment session, the balloon may be deflated (636) and withdrawn from the carotid sinus (638).

Some methods may additionally comprise implanting a baroreceptor stimulator after shock wave treatment, as may be desirable. For example, if a practitioner determines that modulating the activity of the baroreceptors of the carotid sinus (e.g., stimulating and/or increasing activation of the carotid sinus baroreceptors) substantially reduces the patient's blood pressure, s/he may prescribed long-term activation of the baroreceptors (e.g., by implanting a stimulation device) as part of the treatment plan for alleviating symptoms of hypertension.

While this invention has been particularly shown and described with references to embodiments thereof, it will be understood by those skilled in the art that various changes in form and details may be made therein without departing from the scope of the invention. For all of the embodiments described above, the steps of the methods need not be performed sequentially.

What is claimed as new and desired to be protected by Letters Patent of the United States is:

1. A method for nerve therapy comprising:
    advancing a shock wave device within a renal artery, wherein the shock wave device comprises an elongate body having a guide wire lumen, and a shock wave generator coupled to the elongate body; and
    initiating a shock wave from the shock wave generator at a first location in the renal artery adjacent to a renal plexus to impinge upon a wall of the renal artery to at least partially block activation of a renal plexus and wherein the shock wave device further comprises a balloon sealably enclosing a portion of the elongate body, and wherein the shock wave generator is located within the balloon, and wherein the method further comprises inflating the balloon with a liquid before initiating a shock wave from the shock wave generator.

2. The method of claim 1, further comprising initiating a plurality of shock waves at the first location in the renal artery.

3. The method of claim 1, further comprising initiating a shock wave from the shock wave generator at a second location in the renal artery.

4. The method of claim 3, wherein initiating a shock wave at a second location comprises moving the shock wave generator along a longitudinal axis of the elongate body from the first location to the second location.

5. The method of claim 4, wherein initiating a shock wave at a second location comprises rotating the shock wave generator around a longitudinal axis of the elongate body from the first location to the second location.

6. The method of claim 1, wherein initiating a shock wave at the second location comprises:
    deflating the balloon;
    moving the shock wave device to the second location;
    inflating the balloon with a liquid; and
    initiating a shock wave from the shock wave generator at the second location.

7. The method of claim 1, wherein the shock wave generator comprises at least one electrode.

8. The method of claim 1, wherein the shock wave device comprises a second shock wave generator, and the first shock wave generator is at the first location and the second shock wave generator is at a second location.

9. The method of claim 8, further comprising initiating a shock wave from the second shock wave generator at the second location.

10. The method of claim 9, wherein a shock wave is initiated at the first location from the first shock wave generator and a shock wave is initiated at the second location from the second shock wave generator at substantially the same time.

11. The method of claim 1, wherein the shock wave generator comprises:
    an insulating layer wrapped around a portion of the elongate body, said layer having a first aperture therein;
    an inner electrode carried within the elongate body and aligned with the first aperture of the insulating layer; and
    an outer electrode mounted on the insulating layer and having a first aperture coaxially aligned with the first aperture in the insulating layer and arranged so that when a voltage is applied across the electrodes, a shockwave will be initiated therebetween.

12. A method for nerve therapy comprising:
    advancing a shock wave device within a carotid sinus, wherein the shock wave device comprises an elongate body having a guide wire lumen, and first and second shock wave generators coupled to the elongate body wherein the first shock wave generator is at a first location and the second shock wave generator is at a second location; and
    initiating shock waves at substantially the same time from both the first and second shock wave generators at said first and second locations in the carotid sinus to impinge upon and activate baroreceptors located in the carotid sinus.

13. The method of claim 12, wherein the shock wave device further comprises a balloon sealably enclosing a portion of the elongate body, and wherein the shock wave generators are located within the balloon, and wherein the method further comprises inflating the balloon with a liquid before initiating a shock wave from the shock wave generator.

14. The method of claim 12, further comprising initiating a plurality of shock waves at both the first and second locations in the carotid sinus.

15. The method of claim 12, wherein the shock wave generators comprises at least one electrode.

16. The method of claim 12, wherein each shock wave generator comprises:
    an insulating layer wrapped around a portion of the elongate body, said layer having a first aperture therein;

an inner electrode carried within the elongate body and aligned with the first aperture of the insulating layer; and an outer electrode mounted on the insulating layer and having a first aperture coaxially aligned with the first aperture in the insulating layer and arranged so that when a voltage is applied across the electrodes, a shockwave will be initiated therebetween.

* * * * *